United States Patent [19]
Pearson et al.

[11] Patent Number: 5,959,106
[45] Date of Patent: Sep. 28, 1999

[54] PREPARATION OF N-ARYLARYLSULFONAMIDE COMPOUNDS

[75] Inventors: Douglas L. Pearson; Timothy J. Adaway, both of Midland, Mich.

[73] Assignee: Dow AgroSciences LLC, Indianapolis, Ind.

[21] Appl. No.: 09/236,961

[22] Filed: Jan. 25, 1999

Related U.S. Application Data

[60] Provisional application No. 60/072,614, Jan. 26, 1998.

[51] Int. Cl.$^6$ .................................................. C07D 487/04
[52] U.S. Cl. .......................... 544/263; 544/215; 544/217; 544/218; 544/219; 546/119
[58] Field of Search ............................................... 544/263

[56] References Cited

U.S. PATENT DOCUMENTS

| | | | |
|---|---|---|---|
| 4,818,273 | 4/1989 | Kleschick et al. | 544/263 |
| 4,910,306 | 3/1990 | McKendry | 544/263 |
| 5,163,995 | 11/1992 | Van Heertum et al. | 544/263 |
| 5,177,206 | 1/1993 | Johnson et al. | 544/263 |
| 5,614,469 | 3/1997 | Arndt et al. | 544/263 |

FOREIGN PATENT DOCUMENTS

WO 98/21178  5/1998  WIPO.

OTHER PUBLICATIONS

A. Acordia et al., *Tetrahedron*, 33, 105–111 (1977).
A. Acordia et al., *Journal Heterocyclic Chemistry*, 12, 333–335 (1975).
J. F. King et al., *Journal of Pure and Applied Chemistry*, 68, 825–830 (1996).

*Primary Examiner*—Mukund J. Shah
*Assistant Examiner*—V Balasubramanian
*Attorney, Agent, or Firm*—Craig E. Mixan; D. Wendell Osborne

[57] ABSTRACT

N-(substituted aryl)[1,2,4]triazoloazinesulfonamide compounds, such as N-(2,6-difluorophenyl)-8-fluoro-5-methoxy[1,2,4]triazolo[1,5-c]pyrimidine-2-sulfonamide, were prepared at a good reaction rate and in good yield by the reaction of a chlorosulfonyl[1,2,4]triazoloazine compound, such as 2-chlorosulfonyl-8-fluoro-5-methoxy[1,2,4]triazolo[1,5-c]pyrimidine, and an arylamine compound, such as 2,6-difluoroaniline, in an organic medium containing a relatively acidic alcohol, such as propylene glycol or 2,2,2-trifluoroethanol.

10 Claims, No Drawings

PREPARATION OF N-ARYLARYLSULFONAMIDE COMPOUNDS

CROSS-REFERENCE TO RELATED APPLICATIONS

This application claims the benefit of U.S. Provisional Application No. 60/072,614, filed Jan. 26, 1998.

BACKGROUND OF THE INVENTION

The present invention relates to a process for the preparation of N-arylarylsulfonamide compounds by the reaction of a chlorosulfonylaryl compound with an arylamine compound.

N-Arylarylsulfonamide compounds, which are important as agricultural and pharmaceutical chemicals, are often difficult to prepare by condensation of the corresponding chlorosulfonylaryl and arylamine compounds. This is particularly the case for the preparation of N-arylarylsulfonamide compounds derived from deactivated arylamine compounds; that is, from arylamine compounds possessing bulky substituents located on a carbon atom adjacent to the amino nitrogen group (ortho substituents) and/or electron attracting substituents. It is also especially the case for the preparation of N-arylarylsulfonamide compounds derived from chlorosulfonylheteroaromatic compounds. The problem has been reported, for example, in the preparation of certain herbicidal N-(substituted phenyl)[1,2,4]triazolo[1,5-c]pyrimidine-2-sulfonamide compounds and related triazolopyrimidinesulfonamide compounds (U.S. Pat. No. 5,163,995). It has been disclosed that some such condensation reactions can be improved by the addition of a molar amount or more of a pyridine base (U.S. Pat. No. 4,818,273), or by the addition of a catalytic combination of pyridine and dimethylsulfoxide (U.S. Pat. Nos. 5,163,995 and 5,177,206). Further, it has been disclosed that such condensation reactions can be improved by first converting the arylamine compound to an N-trialkylsilylarylamine derivative (U.S. Pat. No. 4,910,306). The problem of slow reaction rates and poor yields persists, however, and improved methods of condensing chlorosulfonylaryl compounds with poorly reactive arylamine compounds that produce the desired N-arylarylsulfonamide compounds rapidly and in good yield would be of considerable value.

The condensation of 2-chlorosulfonylthiophene with aniline and some meta and para substituted anilines was disclosed by A. Arcoria et al. in *Journal of Heterocyclic Chemistry*, 12, 333–335 (1975) and in *Tetrahedron*, 33, 105–111 (1977) to be faster in certain simple alcohol solvents than in certain dipolar aprotic solvents. No yield information was given.

SUMMARY OF THE INVENTION

It has now been found that the condensation of chlorosulfonylaryl compounds and arylamine compounds to form N-arylarylsulfonamide compounds takes place rapidly and in good yield when the reaction is carried out in a medium containing an alcohol solvent having a pKa in water below 15.5 (the pKa of methanol). The resulting reaction is the basis for an improved process for the preparation of N-arylarylsulfonamide compounds.

The process of the invention includes a process for the preparation of N-(substituted aryl)[1,2,4]triazoloazinesulfonamide compounds of Formula I:

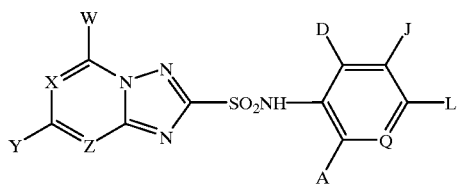

wherein
X and Q each independently represents N or C—H;
Z represents N or C-T;
W, Y, and T each independently represents H, $C_1$–$C_4$ alkyl, $C_1$–$C_4$ alkoxy, F, Cl, Br, $CF_3$, $CF_2H$, $CFH_2$, $CH_2OCH_3$, CN, or $CO_2(C_1$–$C_4$ alkyl);
A, D, J, and L each independently represents H, F, Cl, Br, $C_1$–$C_4$ alkyl, $C_1$–$C_4$ alkoxy, $CF_3$, CN, or $CO_2(C_1$–$C_4$ alkyl), with the proviso that at least one of A and D represents F which comprises contacting a chlorosulfonylaryl compound of Formula II:

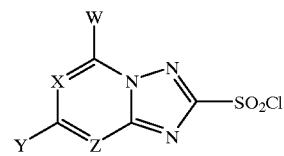

wherein W, X, Y, and Z are defined as for compounds of Formula I
with an arylamine compound of Formula III:

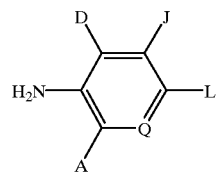

wherein Q, A, D, J, and L are defined as for compounds of Formula I
in an organic solvent medium containing an alcohol that has a pKa in water of less than 15.5, the alcohol in the medium being about 0.3 to about 5 parts per part by weight of the chlorosulfonylaryl compound, at a temperature of about 0° C. to about 100° C.

It is often preferred to use alcohols of Formula IV:

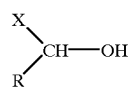

wherein
$X^1$ represents $CH_2F$, $CHF_2$, $CF_3$, $CH_2Cl$, $CHCl_2$, $CCl_3$, $CF_2CH_3$, $CH_2OH$, $CH(OH)CH_3$, $CH_2OCH_3$, or $CH_2CN$; and
R represents H, $CH_3$, or $CH_2F$.
as the alcohol portion the solvent in the process. 1,2-Propanediol (propylene glycol) is often a more preferred alcohol.

The process is particularly useful for the preparation of N-(substituted aryl)[1,2,4]triazoloazinesulfonamide compounds of Formula I wherein Q represents C—H, A represents F, D represents H, F, Cl, $OCH_3$, $CF_3$, or $CO_2CH_3$, J represents H or $CH_3$, and L represents H. It is, further, particularly useful for the preparation of N-(substituted aryl)[1,2,4]triazoloazinesulfonamide compounds of Formula I wherein W represents OCH$_3$ or OCH$_2$CH$_3$, X represents N, Y represents H or CH$_3$, and Z represents C-T wherein T represents H, F, Cl, or OCH$_3$.

DETAILED DESCRIPTION OF THE INVENTION

The process of the invention is useful for the preparation of a wide variety of N-arylarylsulfonamide compounds wherein the term 'aryl' in both instances is defined as aromatic hydrocarbyl and aromatic heterocyclyl moieties, both of which can be substituted. The N-arylarylsulfonamide compounds produced are variously useful as agricultural and pharmaceutical products. The process is especially useful for the preparation of herbicidal N-(substituted aryl)[1,2,4]triazoloazinesulfonamide compounds of Formula I.

The N-arylarylsulfonamide compounds of Formula I:

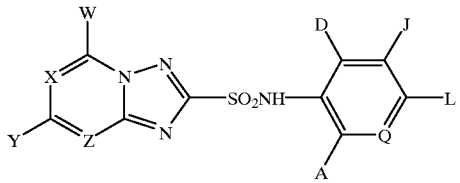

prepared by the process of the invention include N-(substituted aryl)[1,2,4]triazoloazinesulfonamide compounds wherein the [1,2,4]triazoloazine moiety is a [1,2,4]triazolo[1,5-a]pyrimidine, [1,2,4]triazolo[1,5-c]pyrimidine, [1,2,4]triazolo[1,5-a]pyridine, or [1,2,4]triazolo[1,5-a][1,3,5]triazine moiety. That is, the ring members X and Z of Formula I can be either nitrogen or a carbon function: C—H in the case of X and C-T wherein T represents hydrogen, alkyl of 1 to 4 carbons, alkoxy of 1 to 4 carbons, fluoro, chloro, bromo, trifluoromethyl, difluoromethyl, monofluoromethyl, methoxymethyl, cyano, or alkoxycarbonyl having 1 to 4 carbon atoms in the alkoxy portion in case of Z. N-(substituted aryl)[1,2,4]triazoloazinesulfonamide compounds wherein the [1,2,4]triazoloazine moiety is a [1,2,4]triazolo[1,5-c]-pyrimidine moiety are often preferred. The [1,2,4]triazoloazine moiety can be further substituted with common substituents and the compounds of Formula I include compounds wherein W and Y independently represent hydrogen, alkyl of 1 to 4 carbons, alkoxy of 1 to 4 carbons, fluoro, chloro, bromo, trifluoromethyl, difluoromethyl, monofluoromethyl, methoxymethyl, cyano, or alkoxycarbonyl having 1 to 4 carbon atoms in the alkoxy portion. Compounds wherein W, Y, and T represent hydrogen, methoxy, ethoxy, methyl, fluoro, and chloro are often preferred. Compounds wherein W represents methoxy or ethoxy, Y represents H, fluoro, chloro, or methyl, and Z represents C-T wherein T represents hydrogen, fluoro, chloro, or methoxy are often more preferred and compounds wherein X represents N, W represents methoxy or ethoxy, Y represents H, fluoro, chloro, or methyl, and Z represents C-T wherein T represents hydrogen, fluoro, chloro, or methoxy are typically most preferred. The compound N-(2,6-difluorophenyl)-8-fluoro-5-methoxy[1,2,4]triazolo[1,5-c]pyrimidine-2-sulfonamide is often of special interest. The [1,2,4]triazoloazine moiety of the chlorosulfonyl[1,2,4]triazoloazine starting material compounds of Formula II:

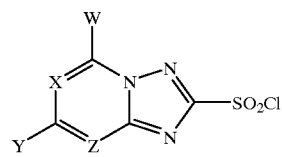

are correspondingly defined and the same preferences pertain.

The N-arylarylsulfonamide compounds of Formula I prepared by the process of the invention further include N-(substituted aryl)[1,2,4]triazoloazinesulfonamide compounds wherein the (substituted aryl) moiety is an optionally further substituted 2- or 6-fluoro or 2,6-difluoroaniline or a 2- or 4-fluoro or 2,4-difluoro-3-aminopyridine moiety. These N-aryl moieties are derived from the arylamine compounds of Formula III:

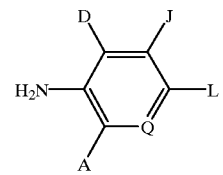

which are 2- or 6-fluoroaniline or 2,6-difluoroaniline or are 2- or 4-fluoro-3-aminopyridine or 2,4-difluoro-3-aminopyridine compounds. In the compounds of Formula I and Formula III, one of the ortho substituents A and D is fluoro and the other is selected from hydrogen, fluoro, chloro, bromo, an alkyl group having 1 to 4 carbon atoms, an alkoxy group having 1 to 4 carbon atoms, trifluoromethyl, cyano, and an alkoxycarbonyl group having 1 to 4 carbons in the alkoxy portion. The meta and para substituents J and L are also is selected from hydrogen, fluoro, chloro, bromo, an alkyl group having 1 to 4 carbon atoms, an alkoxy group having 1 to 4 carbon atoms, trifluoromethyl, cyano, and an alkoxycarbonyl group having 1 to 4 carbons in the alkoxy portion. The ring member Q represents C—H or N; that is, the aromatic nucleus is benzene or pyridine. Benzene compounds are generally preferred. Compounds of Formula I and III wherein A represents fluoro, D represents hydrogen, fluoro, chloro, methoxy, trifluoromethyl, or methoxycarbonyl, J represents hydrogen or methyl, and L represent hydrogen are generally preferred. Compounds wherein Q represents C—H, A and D represent fluoro, J represents hydrogen or methyl, and L represents hydrogen are generally more preferred.

The chemical reaction of the process of the present invention is the condensation of an chlorosulfonylaromatic compound with an aromatic amine compound to form an N-arylarylsulfonamide compound and includes the condensation of chlorosulfonyl[1,2,4]triazoloazine compounds of Formula II with arylamine compounds of Formula III to form N-(substituted aryl)[1,2,4]triazoloazinesulfonamide compounds of Formula I. This reaction has been found to proceed rapidly and in high yield when carried out in the presence of an alcohol having a pKa that is below that of methanol; that is, in the presence of an alcohol that is more acidic than methanol and, accordingly, has a pKa of less than about 15.5. Alcohols having a pKa of less than about 15.5 have been found to accelerate the condensation of a chlorosulfonyl[1,2,4]triazoloazine compound of Formula II with an arylamine compound of Formula III and to give good yields of the desired N-(substituted aryl)[1,2,4]

triazoloazinesulfonamide compounds of Formula I. Simple alcohols, such as methanol, ethanol, and 2-propanol either do not accelerate the reaction sufficiently or are, themselves, too reactive with the chlorosulfonyl[1,2,4]triazoloazine compound of Formula II (to produce alkoxysulfonyl[1,2,4] triazoloazine compounds) and do not give good yields. Stable alcohols that possess an electron withdrawing (σ* greater than 0.49, the value for hydrogen) substituent or combination of substituents on the carbon atom bearing the hydroxy group are usually more acidic than methanol as are diol compounds wherein the two hydroxy groups are vicinal. Preferred alcohols include those of Formula IV:

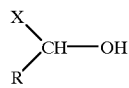

wherein $X^1$ represents fluoromethyl, difluoromethyl, trifluoromethyl, chloromethyl, dichloromethyl, trichloromethyl, 1,1-difluoroethyl, hydroxymethyl, 1-hydroxyethyl, methoxymethyl, or cyanomethyl and R represents hydrogen, methyl, or fluoromethyl. 1,2-Propanediol (propylene glycol), 1,2-ethanediol (ethylene glycol), and 2,2,2-trifluoroethanol are often more preferred. 1,2-Propanediol is often of special interest because of its performance in the process, its low cost, and its low toxicity.

The alcohol of Formula IV employed can be used alone as the organic solvent medium or can be part of an organic solvent medium that includes other alcohols of Formula I and/or inert organic solvents. Inert solvents that can be employed in conjunction with the alcohols of the invention include chlorinated aliphatic solvents, such as dichloromethane, 1,2-dichloroethane, tetrachloroethylene, chloroform, and 1,1,1-trichloroethane; chlorinated aromatic solvents, such as 1,2-dichlorobenzene; aromatic hydrocarbons, such as benzene, toluene, and xylene; nitrites, such as acetonitrile; esters, such as ethyl acetate; and ethers, such as 1,2-dimethoxyethane and tetrahydrofuran. Inert organic solvents in which the chlorosulfonyl[1,2,4] triazoloazine compounds of Formula II are at least somewhat soluble are generally preferred (when an inert organic solvent is used) and dichloromethane is typically more preferred. It is often preferred carry out the process in the presence of the alcohol as the only organic solvent in the medium; that is, without the addition of other inert organic solvents.

The amount of organic solvent medium employed is an amount that facilitates mixing and contact of the reagents as well as heat transfer and that supplies an appropriate amount of the alcohol of Formula IV in relationship with the amount of chlorosulfonyl[1,2,4]-triazoloazine compound of Formula II being condensed. An amount of alcohol sufficient to give a suitably rapid reaction rate, but not so much as to create a problem in product isolation or extra cost in recycle efforts should be employed. The reaction rate typically increases as the amount of alcohol in the system increases, but recovery of the desired product becomes more difficult and expensive. An appropriate amount of the alcohol of Formula IV is generally from at least about 0.3 parts to about 5 parts by weight of alcohol per part of chlorosulfonyl[1,2,4]triazoloazine compound of Formula II used. Amounts between about 0.5 and about 3.0 are generally more preferred.

The amount of arylamine compound of Formula III used in the process of the invention is typically an amount sufficient 1) to react with all of the chlorosulfonyl[1,2,4]triazoloazine compound of Formula II present, 2) to accept all of the hydrogen chloride produced thereby, and 3) some excess. An amount between about 2 moles and about 8 moles per mole of the chlorosulfonyl[1,2,4]triazoloazine compound of Formula II used is preferred and an amount between about 2.2 moles and about 5 moles is typically more preferred. The excess arylamine compound of Formula III and that used to accept the by-product hydrogen chloride are typically recovered and recycled in the process.

The process of the invention is generally carried out at temperatures between about 0° C. and about 100° C. The reaction is typically too slow at temperatures below 0° C. and undesirable side reactions are typically observed at temperatures above 100° C. It is often preferred to carry out the reaction at temperatures between about 20° C. and about 60° C. and more preferred at temperatures between 30° C. and about 45° C., especially when the reactants and products contain substituents that are marginally stable under the reaction conditions. Methoxy substituents in the 5-position of the [1,2,4]triazoloazine ring of the compounds of Formulas I and III (W represents methoxy) are examples. The process is not sensitive to pressure and is usually carried out at or slightly above atmospheric pressure.

The chlorosulfonyl[1,2,4]triazoloazine compound of Formula II, arylamine compound of Formula III, alcohol of Formula IV, and optional inert organic solvent can be combined in any order. It is, however, often preferred to add the chlorosulfonyl[1,2,4]triazoloazine compound slowly to a mixture of the arylamine compound in the alcohol medium. It is, additionally, sometimes preferred to add the alcohol to a mixture of the chlorosulfonyl[1,2,4]triazoloazine compound and arylamine compound. In any event, the combination is optimally made with good mixing to promote the intimate contact of the reagents and with means to exclude moisture from the system. The chemical reaction of the process is typically essentially complete in about 1 to about 12 hours.

The compounds of Formula I produced in the process of the invention can be recovered by conventional means. N-(Substituted aryl)[1,2,4]triazoloazinesulfonamide compounds of Formula I are often insoluble in the organic solvent medium and can be recovered by filtration or centrifugation. The mixture is generally cooled before this operation to minimize the loss of product due to solubility. The product can also be diluted with water to reduce the solubility of the compound of Formula I, especially when the organic solvent medium does not contain an auxiliary inert organic solvent. Alternatively, the alcohol of Formula IV and/or any inert organic solvent can be partially or completely removed by evaporation to reduce the amount of product of Formula I in solution before filtration or centrifugation. The crude insoluble solid products of Formula I obtained are generally extracted with an alcohol solvent and/or water and/or dilute aqueous acid to remove any remaining excess arylamine compound of Formula II and its hydrochloride salt and to remove sulfonic acid or ester by-products. The N-(substituted aryl)[1,2,4] triazoloazinesulfonamide compounds of Formula I prepared by the process of the invention and recovered in this manner are typically of very high purity; assays of over 99 percent are common.

EXAMPLES

1. Preparation of N-(2,6-Difluorophenyl)-8-fluoro-5-methoxy[1,2,4]triazolo[1,5-c]pyrimidine-2-sulfonamide A jacketed 250 mL (milliliter) round bottom flask equipped with a stirrer, condenser, and nitrogen inlet and outlet was loaded with 49.1 g (grams), 0.38 mol (mole) of 2,6-difluoroaniline and 25 g of 1,2-propanediol. The mixture was warmed to 35° C. by heating the jacket fluid and a solution of 30.3 g of 93 percent purity (0.10 mol) of 2-chlorosulfonyl-8-fluoro-5-methoxy[1,2,4]triazolo[1,5-c]pyrimidine in 30.2 g of dichloromethane was added portionwise with stirring under a nitrogen blanket over 3.5 hours. A solid began to form in about one hour and all of the chlorosulfonyl starting material was consumed in 5.5 hours. The resulting mixture was cooled to 20° C. and filtered, collecting the solids. The solids were washed 2×40 mL with methanol and then with 112 g of water. The white solid obtained after drying was found to be the title compound with a purity of greater than 99 percent and to amount to 34.2 g (88.9 percent of theory).

2. Preparation of N-(2,6-Difluorophenyl)-8-fluoro-5-methoxy[1,2,4]triazolo[1,5-c]pyrimidine-2-sulfonamide in the Presence of Catalytic Alcohols A. A 4.8 g (18 mmol) sample of 2-chlorosulfonyl-8-fluoro-5-methoxy[1,2,4]triazolo[1,5-c]pyrimidine was placed in a 50 mL round bottom flask and then the following were added with stirring under nitrogen: 10 mL of an alcohol solvent, 12.9 g (100 mmol) of 2,6-difluoroaniline, and a few crystals of naphthalene (liquid chromatography internal standard). The mixture was heated to the desired temperature and the disappearance of the chlorosulfonyl starting material was monitored by high pressure liquid chromatography. When the reaction was complete, the mixture was cooled to 0 to 5° C. over a 30-min period and the solids were recovered by filtration, washed with cold solvent, washed with 0.5 N aqueous hydrochloric acid, and dried. The recovered title compound product was over 99 percent pure. The results are given as Runs 1 to 3 in the table below.

B. A solution of 5.1 g (40 mmol) of 2,6-difluoroaniline, 10 mL of alcohol solvent and a few crystals of naphthalene (liquid chromatography internal standard) was placed in a 50 mL flask and heated to 40° C. Solid 2-chlorosulfonyl-8-fluoro-5-methoxy[1,2,4]triazolo[1,5-c]pyrimidine (2.67 g, 10 mmol) was added with stirring under nitrogen and the disappearance of the chlorosulfonyl starting material was monitored by high pressure liquid chromatography. The mixture was cooled to ambient temperature and the solids were recovered by filtration, washed with 10 mL of 2-propanol and then water, and dried. The recovered title compound product was over 99 percent pure. The results are given as Runs 4 to 6 in the following table.

| Run No. | Alcohol Solvent | Temp., °C. | Time, hours | Actual Yield, % | Recovered Yield, % |
|---|---|---|---|---|---|
| 1 | 2,2,2-trichloro-ethanol | 45 | 2 | 94 | 82 |
| 2 | 2,2,2-trifluoro-ethanol | 40 | 2.5 | 89 | 68 |
| 3 | 2-methoxyethanol | 3 | 30 | 90 | 67 |
| 4 | 1,2-ethanediol | 40 | 1.5 | 97 | 83 |
| 5 | 1,2-propanediol | 40 | 1.5 | 98 | 88 |
| 6 | 2-methoxyethanol | 40 | 3 | 93 | 68 |

3. Preparation of N-(2,6-Difluorophenyl)-8-fluoro-5-methoxy[1,2,4]triazolo[1,5-c]pyrimidine-2-sulfonamide in the Presence of 1,2-Propanediol The preparation of the title compound was carried out as in Example 1 except that some of the parameters were varied. When the reaction was carried out at 25, 35, and 45° C., the time to complete disappearance of 2-chlorosulfonyl-8-fluoro-5-methoxy[1,2,4]triazolo[1,5-c]pyrimidine and the recovered yield of title compound were 6.5 hours/86.5 percent of theory, 5.5 hours/87.9 percent of theory, and 4.9 hours/84.6 percent of theory, respectively. When the amount of 1,2-propanediol was 1.88, 0.95, and 0.48 grams per gram of 2-chlorosulfonyl-8-fluoro-5-methoxy[1,2,4]triazolo[1,5-c]-pyrimidine, the time to complete disappearance of the latter was 3, 5, and 8 hours, respectively.

4. Preparation of N-(2,6-Difluorophenyl)-7-fluoro-5-ethoxy[1,2,4]triazolo[1,5-c]pyrimidine-2-sulfonamide A solution of 19.9 g of 90 percent pure 2-chlorosulfonyl-7-fluoro-5-ethoxy[1,2,4]triazolo[1,5-c]-pyrimidine (64 mmol) in 20 g of dichloromethane was prepared and combined with 28.9 g of 97 percent pure 2,6-difluoroaniline (218 mmol) and 14.9 g of 1,2-propanediol. The mixture, which appeared to be slightly exothermic initially, was heated with stirring at 35° C. for 3 hours. It was then cooled to 20° C. and filtered to recover the solids, which were then washed with 2×30 mL of methanol and air dried to obtain 18.4 g (68.4 percent of theory) of the title compound as a white solid. The filtrate was analyzed by high pressure liquid chromatography and found to contain 4.5 g (17 percent of theory) of the title compound. The total yield was, accordingly, 85 percent. The identity of the product was verified by comparison with standards.

5. Preparation of N-(4-Chloro-2,6-difluorophenyl)-8-fluoro-5-methoxy[1,2,4]triazolo[1,5-c]pyrimidine-2-sulfonamide A mixture of 24.0 g (147 mmol) of 4-chloro-2,6-difluoroaniline and 22.9 g of 1,2-propanediol was placed in a round bottom flask and heated to 35° C. with stirring. A mixture of 14.5 g (49 mmol) of 88 percent purity 2-chlorosulfonyl-8-fluoro-5-methoxy[1,2,4]triazolo[1,5-c]pyrimidine with 29.1 g of dichloromethane was prepared and was added in 1 mL shots over a 4 hour period. The resulting mixture was heated another 4 hours and was then stirred overnight at ambient temperature. It was then cooled to about 20° C. and filtered, collecting the solids present. The solids were slurried in 30 mL of a 1:1 mix of 2-propanol and water, collected by filtration, washed with 2×30 mL of 2-propanol, and air dried to obtain 14.8 g (75 percent of theory) of the title compound as a white powder of 98 percent purity melting at 203–204° C.

6. Preparation of N-(2-Fluorophenyl)-8-fluoro-5-methoxy[1,2,4]triazolo[1,5-c]pyrimidine-2-sulfonamide A mixture of 12.5 g (46.9 mmol) of 2-chlorosulfonyl-8-fluoro-5-methoxy[1,2,4]triazolo[1,5-c]pyrimidine and 25 mL of 1,2-propanediol was placed in a round bottom flask and cooled to 5° C. under nitrogen. 2-Fluoroaniline (13.7 g, 123 mmol) was added with stirring and cooling over a 10-min period. There was an exotherm. The mixture was allowed to warm to ambient temperature with stirring overnight and was then diluted with 30 mL of water. The mixture was stirred for 30 min and the solids present were then collected by filtration, washed with 2×25 mL of water and 2×25 mL of 2-propanol. The resulting solid was recrystallized from about 175 mL of 2-propanol and dried under reduced pressure at 45° C. to obtain 13.2 g (82.5 percent of theory) of the title compound as a white solid of 99 percent purity. The structure of this compound was confirmed by its proton nuclear magnetic resonance spectrum (300 MegaHertz, D-6 acetone): 9.70(s, 1H), 8.17(d, 1H, J=1.9 Hertz), 7.58(m, 1H), 7.24(m, 1H), 7.16(m, 2H), 4.29(s, 3H) and its C-13 carbon nuclear magnetic resonance spectrum (75 MegaHertz, D-6 acetone): 165.6, 156.8(d, J=244.8 Hertz), 149.1(d, J=26.1), 147.8, 145.7(d, J=252.9), 130.2(d, J=21.8), 128.5(d, J=4.1), 125(m), 116.7(d, J=19.7), 57.6.

What is claimed is:

1. A process for the preparation of N-(substituted aryl)[1,2,4]triazoloazinesulfonamide compounds of the formula:

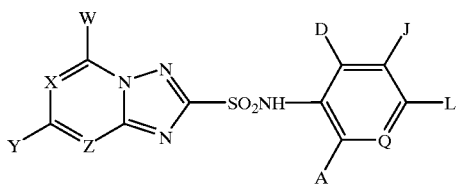

wherein
X and Q each independently represents N or C—H;
Z represents N or C-T provided that when X is N, Z is not N and when X is C—H, Z is not C-T;
W, Y, and T each independently represents H, $C_1$–$C_4$ alkyl, $C_1$–$C_4$ alkoxy, F, Cl, Br, $CF_3$, $CF_2H$, $CFH_2$, $CH_2OCH_3$, CN, or $CO_2(C_1$–$C_4$ alkyl);
A, D, J, and L each independently represents H, F, Cl, Br, $C_1$–$C_4$ alkyl, $C_1$–$C_4$ alkoxy, $CF_3$, CN, or $CO_2(C_1$–$C_4$ alkyl), with the proviso that at least one of A and D represents F which comprises contacting a chlorosulfonylaryl compound of the formula:

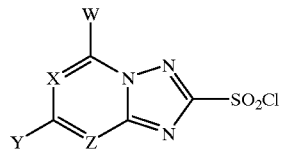

wherein W, X, Y, and Z are defined as before with an arylamine compound of the formula:

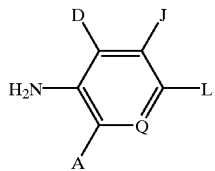

wherein Q, A, D, J, and L are defined as before
in an organic solvent medium containing an alcohol that has a pKa in water of less than 15.5, the alcohol in the medium being about 0.3 to about 5 parts per part by weight of the chlorosulfonylaryl compound, at a temperature of about 0° C. to about 100° C.

2. A process according to claim 1 wherein the alcohol in the organic solvent medium is an alcohol of the formula:

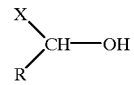

wherein
$X^1$ represents $CH_2F$, $CHF_2$, $CF_3$, $CH_2Cl$, $CHCl_2$, $CCl_3$, $CF_2CH_3$, $CH_2OH$, $CH(OH)CH_3$, $CH_2OCH_3$, or $CH_2CN$; and
R represents H, $CH_3$, or $CH_2F$.

3. A process according to claim 2 wherein the alcohol is 1,2-propanediol, 1,2-ethanediol, or 2,2,2-trifluoroethanol.

4. A process according to claim 3 wherein the alcohol is 1,2-propanediol.

5. A process according to claim 1 wherein Q represents C—H, A represents F, D represents H, F, Cl, $OCH_3$, $CF_3$, or $CO_2CH_3$, J represents H or $CH_3$, and L represents H.

6. A process according to claim 1 wherein W represents $OCH_3$ or $OCH_2CH_3$, X represents N, Y represents H, F, Cl, or $CH_3$, and Z represents C-T wherein T represents H, F, Cl, or $OCH_3$.

7. A process according to claim 1 wherein W represents $OCH_3$, X represents N, each of Y, J, and L represents H, Z represents C—F, Q represents C—H, and each of A and D represents F.

8. A process according to claim 1 wherein the temperature is about 20 to about 60° C.

9. A process according to claim 1 wherein the weight of the alcohol is about 0.5 to about 3 parts per part by weight of the chlorosulfonylaryl compound.

10. A process for preparing N-(2,6-difluorophenyl)-8-fluoro-5-methoxy[1,2,4]triazolo[1,5-c]pyrimidine-2-sulfonamide which comprises contacting 2-chlorosulfonyl-8-fluoro-5-methoxy[1,2,4]triazolo[1,5-c]pyrimidine with 2,6-difluoroaniline in an organic solvent medium containing about 0.5 to about 3 parts by weight of 1,2-propanediol per part of 2-chlorosulfonyl-8-fluoro-5-methoxy[1,2,4]triazolo[1,5-c]pyrimidine at a temperature of about 30° C. to about 45° C.

* * * * *